(12) United States Patent
Merchant et al.

(10) Patent No.: US 12,325,428 B2
(45) Date of Patent: Jun. 10, 2025

(54) SYSTEMS AND METHODS FOR IN-FLIGHT HEALTH MONITORING AND COMFORT TRACKING

(71) Applicant: Honeywell International Inc., Charlotte, NC (US)

(72) Inventors: Shafi Merchant, Bangalore (IN); Murali Kusuma, Hyderabad (IN); Sreenivas Venkataramappa, Bengaluru (IN); R Jagadeesh Uma Shankar, Bangalore (IN)

(73) Assignee: Honeywell International Inc., Charlotte, NC (US)

( * ) Notice: Subject to any disclaimer, the term of this patent is extended or adjusted under 35 U.S.C. 154(b) by 189 days.

(21) Appl. No.: 18/159,186

(22) Filed: Jan. 25, 2023

(65) Prior Publication Data
US 2024/0190440 A1    Jun. 13, 2024

(30) Foreign Application Priority Data
Dec. 8, 2022    (IN) .............................. 202211070887

(51) Int. Cl.
*B60W 40/08*    (2012.01)
*A61B 5/00*    (2006.01)

(52) U.S. Cl.
CPC ........... *B60W 40/08* (2013.01); *A61B 5/6893* (2013.01)

(58) Field of Classification Search
CPC .............................. B60W 40/08; A61B 5/6893
USPC ..................................................... 340/573.1
See application file for complete search history.

(56) References Cited

U.S. PATENT DOCUMENTS

| | | | |
|---|---|---|---|
| 8,022,843 B2 | 9/2011 | Mitchell et al. | |
| 8,548,547 B2* | 10/2013 | Vij ........................... | A61B 5/18 600/323 |
| 8,957,790 B2 | 2/2015 | Cornell et al. | |
| 11,718,327 B1* | 8/2023 | Marcolino Quintao Severgnini ............ | B60W 40/08 701/23 |
| 2002/0154029 A1 | 10/2002 | Watters et al. | |
| 2010/0036269 A1 | 2/2010 | Ferren et al. | |
| 2010/0168527 A1 | 7/2010 | Zumo et al. | |
| 2011/0040156 A1* | 2/2011 | Vij ........................... | A61B 5/18 600/300 |
| 2012/0066726 A1 | 3/2012 | Mondragon et al. | |

(Continued)

FOREIGN PATENT DOCUMENTS

WO    2013187985 A1    12/2013

*Primary Examiner* — Naomi J Small
(74) *Attorney, Agent, or Firm* — Alston & Bird LLP

(57) ABSTRACT

A method of monitoring passenger health and comfort onboard a vehicle, including: transmitting a request to connect to a user device associated with a passenger on the vehicle; receiving a connection confirmation from the user device; obtaining, from one or more sensors associated with the user device, passenger health data; receiving from one or more other sensors onboard the vehicle, environmental data; generating, based on the passenger health data and the environmental data, an indicator value for each of a plurality of parameters; determining whether the indicator value for any of the plurality of parameters has reached a threshold value; generating, responsive to determining that the indicator value has reached the threshold value for any of the plurality of parameters, a recommended action; and automatically transmitting the recommended action to a designated device.

20 Claims, 6 Drawing Sheets

(56) References Cited

U.S. PATENT DOCUMENTS

| | | | |
|---|---|---|---|
| 2014/0275834 A1* | 9/2014 | Bennett | A61B 5/0205 |
| | | | 600/300 |
| 2014/0310739 A1* | 10/2014 | Ricci | G06Q 30/0633 |
| | | | 725/75 |
| 2015/0182130 A1* | 7/2015 | Utter, II | A61B 5/0024 |
| | | | 600/483 |
| 2015/0347971 A1* | 12/2015 | D'Amore | G06Q 10/101 |
| | | | 705/300 |
| 2018/0374368 A1* | 12/2018 | Bolling | B64D 45/04 |
| 2019/0276037 A1* | 9/2019 | Ito | G06T 7/0014 |
| 2020/0249822 A1* | 8/2020 | Penilla | G06F 3/0488 |
| 2022/0198902 A1* | 6/2022 | Yao | G08B 21/043 |
| 2022/0230522 A1* | 7/2022 | Myers | A61B 5/18 |
| 2023/0297123 A1* | 9/2023 | Feyereisen | G05D 1/101 |
| | | | 701/3 |
| 2023/0333197 A1* | 10/2023 | Neal | G08B 25/001 |
| 2024/0071107 A1* | 2/2024 | Kunhiraman | A61B 5/18 |

\* cited by examiner

SYSTEMS AND METHODS FOR IN-FLIGHT HEALTH MONITORING AND COMFORT TRACKING

CROSS-REFERENCE TO RELATED APPLICATION(S)

This application claims the benefit of priority to Indian Application No. 202211070887, filed on Dec. 8, 2022, the entirety of which is incorporated by reference herein.

TECHNICAL FIELD

Various embodiments of the present disclosure relate generally to the field of health and comfort monitoring systems, and, more particularly, to systems and methods for monitoring the health and/or comfort of passengers on an aircraft.

BACKGROUND

Air travel remains a popular form of transportation for many individuals. However, despite the presence of a variety of onboard amenities (e.g., comfortable seats, air conditioning, lighting and entertainment systems, etc.), the travel experience may not always be ideal and may result in some individuals arriving at their destinations tired, jetlagged, and/or dehydrated. Arriving in such a state may not only diminish an individual's appearance and mood, but it may also negatively affect their ability to perform certain tasks (e.g., participate in business meetings, deliver presentations, etc.). It would therefore be desirous to mitigate travel adversities and facilitate smoother destination transitions. Additionally, in situations where an individual's travel hardships extend beyond just discomfort (i.e., those situations in which the individual experiences a real health emergency during travel), it would further be desirous for the crew and/or other passengers (e.g., those passengers with a medical background) to be presented with actionable information to address the health emergency in an effective and timely fashion. Accordingly, given the foregoing, a need exists for a robust and dynamic system that may monitor passenger health and comfort and deliver real-time notifications and recommendations to address passenger needs.

The present disclosure is directed to overcoming one or more of these above-referenced issues. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, systems and methods are disclosed for monitoring the health and comfort of passengers onboard a vehicle and generating event-based notifications upon detecting an abnormality with either of the foregoing.

In one embodiment, a method of monitoring health information and providing recommendation for one or more passengers on a vehicle is disclosed. The method may include: transmitting, from a health monitoring system associated with the vehicle, a request to connect to a user device associated with a passenger on the vehicle; receiving, at the health monitoring system and from the user device, a connection confirmation; obtaining, using the health monitoring system subsequent to receiving the connection confirmation and from one or more sensors associated with the user device, passenger health data; receiving, at the health monitoring system from one or more other sensors onboard the vehicle, environmental data; generating, based on the passenger health data and the environmental data, an indicator value for each of a plurality of parameters; determining, using a processor of the health monitoring system, whether the indicator value for any of the plurality of parameters has reached a threshold value; generating, responsive to determining that the indicator value has reached the threshold value for any of the plurality of parameters, a recommended action; and automatically transmitting the recommended action to a designated device.

In accordance with another embodiment, a computer system for monitoring health information and providing recommendation for one or more passengers is disclosed. The computer system may include: at least on processor; at least one database; and a server in network communication with the at least one database, the server configured to perform operations including: transmitting, from a health monitoring system associated with the vehicle, a request to connect to a user device associated with a passenger on the vehicle; receiving, at the health monitoring system and from the user device, a connection confirmation; obtaining, using the health monitoring system subsequent to receiving the connection confirmation and from one or more sensors associated with the user device, passenger health data; receiving, at the health monitoring system from one or more other sensors onboard the vehicle, environmental data; generating, based on the passenger health data and the environmental data, an indicator value for each of a plurality of parameters; determining, using a processor of the health monitoring system, whether the indicator value for any of the plurality of parameters has reached a threshold value; generating, responsive to determining that the indicator value has reached the threshold value for any of the plurality of parameters, a recommended action; and automatically transmitting the recommended action to a designated device.

In accordance with another embodiment, a non-transitory computer-readable medium storing computer-executable instructions which, when executed by a server in network communication with at least one database, cause the server to perform operations including: transmitting, from a health monitoring system associated with the vehicle, a request to connect to a user device associated with a passenger on the vehicle; receiving, at the health monitoring system and from the user device, a connection confirmation; obtaining, using the health monitoring system subsequent to receiving the connection confirmation and from one or more sensors associated with the user device, passenger health data; receiving, at the health monitoring system from one or more other sensors onboard the vehicle, environmental data; generating, based on the passenger health data and the environmental data, an indicator value for each of a plurality of parameters; determining, using a processor of the health monitoring system, whether the indicator value for any of the plurality of parameters has reached a threshold value; generating, responsive to determining that the indicator value has reached the threshold value for any of the plurality of parameters, a recommended action; and automatically transmitting the recommended action to a designated device.

Additional objects and advantages of the disclosed embodiments will be set forth in part in the description that follows, and in part will be apparent from the description, or may be learned by practice of the disclosed embodiments.

The objects and advantages of the disclosed embodiments will be realized and attained by means of the elements and combinations particularly pointed out in the appended claims. As will be apparent from the embodiments below, an advantage to the disclosed systems and methods is that avionics data may be retrieved efficiently from legacy and resource constrained platforms though a distributed data acquisition process.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
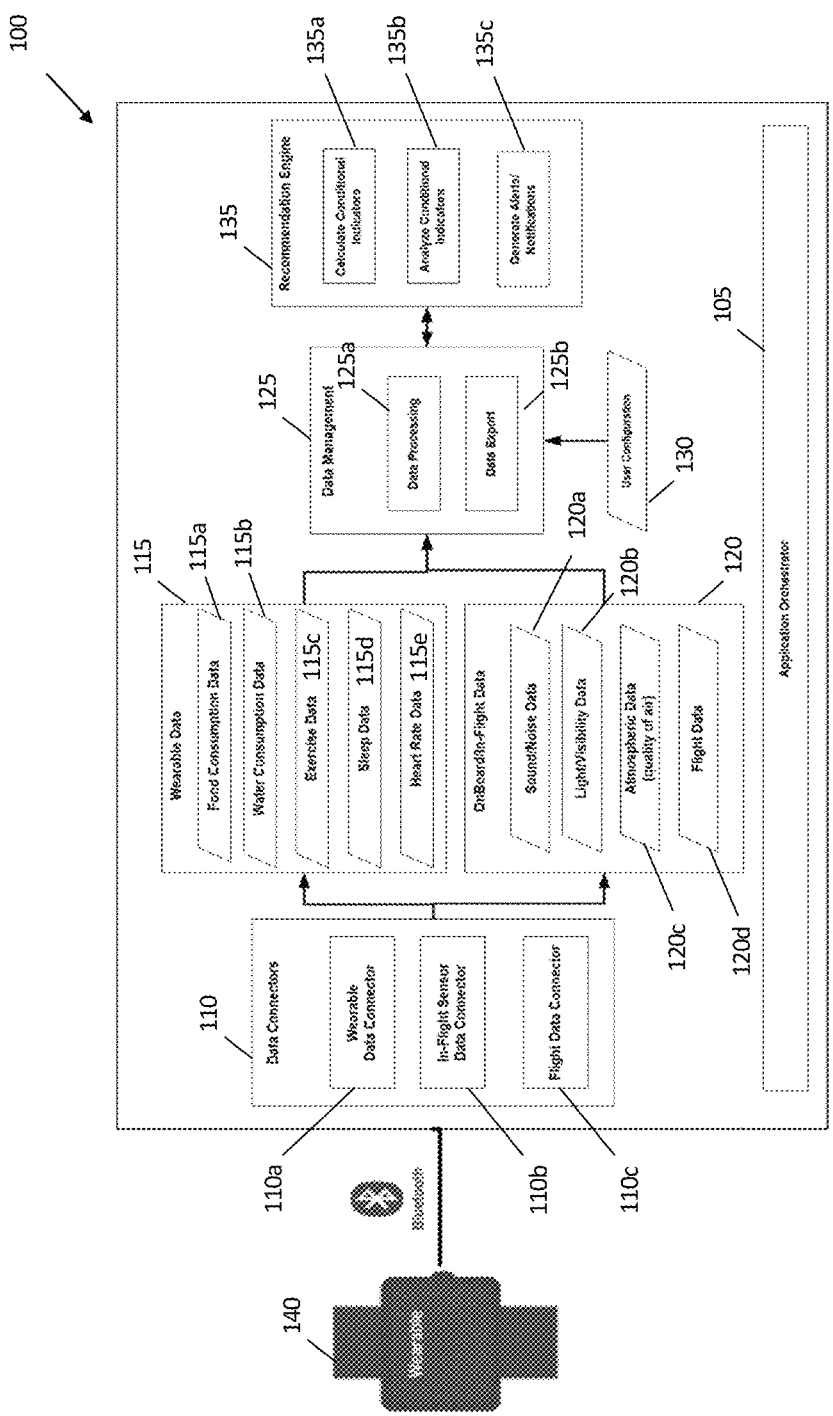
FIG. 1 depicts an application environment, according to one or more embodiments of the present disclosure.

The following embodiments describe systems and methods for improving the monitoring and handling of the health and comfort of passengers in a vehicle. As described above, there is a need for an optimized health and comfort monitoring system that not only ensures that passengers and crew are comfortable during their transit but that also ensures that any health issues that may arise are promptly and effectively responded to. In the context of this application, a "vehicle" may refer to virtually any type of object utilized to transport people or goods, e.g., motor vehicles (e.g., cars, trucks, buses, motorcycles, etc.), railed vehicles (e.g., trains, etc.), amphibious vehicles (e.g., boats, etc.), aircraft (e.g., planes, helicopters, etc.), spacecraft, autonomous or semi-autonomous vehicles, and the like. For simplicity purposes, the vehicle described throughout the remainder of the specification is an airplane. However, it is important to note that this designation is not limiting and the embodiments disclosed herein may be applicable to other vehicle types.

As previously alluded to above, many individuals spend a significant amount of their time traveling, e.g., onboard aircraft. For instance, some businessman spend hundreds of hours per year in an airplane commuting to work, traveling to see clients, etc. Although various amenities exist onboard planes to ease the burdens of travel, no conventional systems or devices exist that are able to effectively monitor passenger well-being and take action to minimize jetlag, fatigue, and/or general discomfort. More particularly, although devices exist today (e.g., wearable fitness trackers, etc.) that are able to monitor the health and fitness of individuals on the ground (e.g., while they are walking and/or sleeping), these devices are not optimized to accurately track and/or consider the well-being of passengers during air travel. For example, although a fitness tracker may be able to identify that a passenger's biometrics (e.g., heart rate, blood pressure, etc.) are within normal ranges while they are seated, it is unable to determine whether or not that individual is actually feeling comfortable and/or rested in their seat. Additionally, in another example, existing devices may be unable to anticipate certain issues (e.g., jetlag) facing passengers upon their arrival at their destination and dynamically take action to minimize the impact of those issues.

Further to the foregoing, it is not uncommon for some passengers to experience a serious health emergency during travel. More particularly, the physical stresses of flight (e.g., resulting from pressure differentials experienced by the human body at altitude, etc.) may exacerbate existing health issues in some at-risk individuals to such a degree that a health emergency may occur. In these situations, attempts may be made to deliver aid to the passenger directly on the aircraft. However, without immediately knowing the health history of the affected passenger, or the potential aid-giving capabilities of other passengers on the flight, the effectiveness of the provided aid may be limited. Furthermore, to address these emergencies, it is common for aircraft to divert away from their original route (e.g., to another airport that may be proximate to a hospital or another medical facility) so that the affected passenger may have access to more robust medical care. However, identifying the ideal airport and new route may be time-consuming and burdensome for the pilots. Additionally, some in-flight emergencies may not be necessary and any instituted diversion may result in travel delays and cost the airline additional resources.

Accordingly, in view of the foregoing, the following embodiments describe systems and methods for monitoring health information and providing recommendations for courses of action that one or more passengers on a vehicle may take to improve passenger health and comfort. According to certain aspects of the present disclosure, one or more integrally or operatively coupled systems and/or devices may be configured to measure, monitor, and ensure that passenger discomfort is minimized during travel. According to other aspects of the present disclosure, a system is provided that may be connected to the avionics of the aircraft. This system may monitor the health of the passengers and suggest immediate actions to take in case of a detected emergency. Such a system may also determine the need to institute a flight diversion and, responsive to determining that such a diversion is needed, may identify the optimal diversion location given the contextual nature of the emergency.

The subject matter of the present description will now be described more fully hereinafter with reference to the accompanying drawings, which form a part thereof, and which show, by way of illustration, specific exemplary embodiments. An embodiment or implementation described herein as "exemplary" is not to be construed as preferred or advantageous, for example, over other embodiments or implementations; rather, it is intended to reflect or indicate that the embodiment(s) is/are "example" embodiment(s). Subject matter can be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The term "or" is meant to be inclusive and means either, any, several, or all of the listed items. The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as, "substantially" and "generally," are used to indicate a possible variation of ±10% of a stated or understood value.

Referring now to the appended drawings, FIG. 1 shows an overview of an exemplary application environment ("environment") according to one or more embodiments of the present disclosure. The environment 100 may include an application orchestrator 105, a data connector component 110, a wearable data component 115, an onboard/in-flight data component 120, a data management component 125, a user configuration component 130, and a recommendation engine 135. In an embodiment, a user device 140 (e.g., a wearable device) may be connectable to the environment 100 via a wireless connection (e.g., BLUETOOTH).

In an embodiment, the application orchestrator 105 may be the driving component of the environment 100 and may be configured to continuously capture data from one or more data broadcasting sensors and/or devices and may also be configured to capture flight details from one or more vehicle systems (e.g., an avionics system of the plane, etc.) utilizing, e.g., the connectors of the data connector component 110. The application orchestrator 105 may then utilize the data management component 125 and recommendation engine 135 to process the received data and to generate and transmit alert notifications based on user configured designations, as further described herein.

In an embodiment, the application orchestrator 105 may leverage a wearable data connector 110a, an in-flight sensor data connector 110b, and/or a flight data connector 110c, contained within the data connector component 110 to capture various types of user metric data, physical environment data, and/or flight data. In an embodiment, the wearable data connector 110a may be configured to receive wearable user data from the user device 140. It is important to note that although the user device 140 is described herein as being a wearable device and that the wearable data connector 110a is described as obtaining data from the wearable device, such a designation is not limiting. More particularly, the user device 140 does not necessarily need to be a wearable device but may be virtually any type of device that is able to capture various types of user metric data. Similarly, the wearable data connector 110a is not necessarily limited to only capturing user metric data from wearable devices, but may also be operable to receive user metric data from other types of non-wearable devices as well.

In an embodiment, the user metric data captured by the wearable data connector 110a may be transmitted to and stored in a wearable data component 115. More particularly, the data connector component 110 may associate all types of data captured by the wearable data connector 110a as user metric data and may thereafter route the user metric data to the wearable data component 115. In an embodiment, non-limiting types of user metric data that may be captured include food consumption data 115a, water consumption data 115b, exercise data 115c, sleep data 115d, heart rate data 115e, and other user metrics that are not explicitly listed here. In an embodiment, each of the foregoing types of user metric data may be captured by one or more sensors integrated within the user device 140 (e.g., camera sensors, ambient light sensors, microphones, gyroscopes, accelerometers, skin temperature sensors, heart rate sensors, multipurpose electrical sensors, altimeters, etc.), input by the user themselves, deduced via leveraging one or more Internet resources, etc.

In an embodiment, the in-flight sensor data connector 110b may be configured to receive data associated with the passenger's cabin environment during flight. More particularly, one or more sensors (e.g., camera sensors, microphones, ambient light sensors, thermopile sensors, etc.) positioned within and/or around the flight cabin may be configured to capture ambient environment data and thereafter transmit that data to the in-flight sensor data connector 110b. Once received by the in-flight sensor data connector 110b, the data connector component 110 may thereafter route the in-flight data to the onboard/in-flight data component 120. Potential types of in-flight data that may be captured and stored include sound/noise data 120a, light/visibility data 120b, atmospheric (air quality) data 120c, flight data 120d, and other data types not explicitly listed here.

In an embodiment, the flight data connector 110c may be configured to connect to a flight operation center database using any available service interface connection (e.g., Internet, Wi-Fi, mobile communication protocols, etc.) to obtain the flight data based on the flight number and/or day of travel. In an embodiment, the flight data may include estimated departure times, designated arrival date, estimated arrival time, and the like. In an embodiment, the flight data connector 110c may be configured to establish the connection with the flight operation center database each time a connection is possible to ensure that the flight data connector 110c is able to obtain the flight data information. In an embodiment, in situations during transit where passengers may be unable to access the Internet, users may still be able to access the foregoing types of flight data via the functionality of the flight data connector 110c. In an embodiment, the captured flight data may be transmitted to and stored in the onboard/in-flight data component 120.

In an embodiment, the data types from the wearable data component 115 and the onboard/in-flight data component 120 may be transmitted to a data management component 125. In an embodiment, the data management component 125 may contain a data processing module 125a at which the data from the wearable data component 115 and the onboard/in-flight data component 120 may be received and processed. More particularly, the data processing module 125a may convert raw data to a more usable format (e.g., by applying metadata tags, etc.).

In an embodiment, a user configuration component 130 may be in communication with and may be configured to transmit user designation data to the data management component 125. More particularly, a user may interact with the application environment 100 (e.g., via a graphical user interface (GUI)) to provide preferences designations to user configuration component 130. These preference designations may include desired ambient sound levels, temperature settings, air quality levels, humidity levels, sleep time preferences, dining time preferences, and the like, and may serve as predetermined, user-designated thresholds that the user has indicated will make them comfortable during travel. Additionally or alternatively, other types of user context data associated with the user may be dynamically predicted by the environment 100 and stored in the user configuration component 130. For instance, the environment 100 may leverage the knowledge obtained by the flight data connector 110c (e.g., flight time, destination time zone, anticipated landing time, etc.) to generate a jetlag/fatigue index that estimates the user's projected level of jetlag and/or fatigue when they arrive at their destination.

In an embodiment, the processed data from the wearable data component 115 and the onboard/in-flight data component 120 may be combined with the user designation data obtained from the user configuration component 130 into a master data set, which may subsequently be provided to and processed by a recommendation engine 135, as further described below.

In an embodiment, the recommendation engine 135 may be configured to generate alerts/notifications related to passenger health and comfort based on user configured designations. More particularly, the recommendation engine 135 may compare the user metric data and the onboard/inflight data with the user designation data and user context data to determine whether values for various user health and/or comfort parameters fall below a predetermined threshold. Responsive to determining that they do, the recommendation engine 135 may generate alerts that provide an indication of this event. In an embodiment, these alerts may thereafter be communicated back to the data management component 125 and subsequently exported by the data export module 125b to one or more designated devices (e.g., to a flight crewmember device, to a device associated with an aviation fitness consultant, to a device associated with the aircraft pilot, etc.) in an attempt to dynamically mitigate passenger discomfort without requiring additional action from the passenger. In an embodiment, each of these alerts may, for example, identify the relevant passenger for which the alert was generated, provide an indication of the particular parameter(s) for the relevant passenger that have fallen below the predetermined threshold, and provide one or more recommendations for ways that the parameter value(s) may be adjusted back to a normal/optimal range.

In an embodiment, the recommendation engine 135 may be composed of three separate modules, i.e., a conditional indicator calculation module 135a, a conditional indicator analysis module 135b, and an alert/notification generator module 135c. These three modules may operate together generate the notification alerts, as further described below.

In the conditional indicator calculation module 135a, data obtained from the wearable data component 115 and the onboard/in-flight data component 120 may be combined and/or individually processed to generate indicator values for each user-designated parameter. For example, using temperature data as a representative parameter, the conditional indicator calculation module 135a may be able to process all user body temperature information obtained from the wearable data component 115 as well as ambient cabin temperature information obtained from the onboard/in-flight data component 120 to identify a user body temperature value and/or a current cabin temperature value. Additionally or alternatively, the conditional indicator calculation module 135a may identify historical extreme and average temperature values associated with the user and/or the flight cabin (e.g., a historical minimum temperature in the cabin, a historical maximum temperature in the cabin, an average overall cabin temperature, an average cabin temperature at different stages of flight, an extreme user body temperature, an average user body temperature, etc.) and determine where the user's current body temperature and/or the current cabin temperature fall on the historical cabin temperature scale.

In the conditional indicator analysis module 135b, each calculated indicator value may be analyzed to determine whether the indicator value has exceeded a predetermined, user-designated threshold value for a particular parameter. In an embodiment, as previously disclosed, the designation of the predetermined threshold value and/or may be established by a user via interaction with the user configuration component 130. For example, a passenger may specify that they do not feel comfortable if the temperature in the cabin during flight is below a predetermined temperature threshold. Upon identifying that a current cabin temperature proximate to the passenger's location in the plane is below the predetermined threshold temperature, then the recommendation engine 135 may leverage the alert/notification generator module 135c to generate an alert/notification, as further described below.

In the alert/notification generator module 135c, alerts/notifications may be generated that provide indications of the results obtained from the analysis conducted by the conditional indicator analysis module 135b. In an embodiment, these alert/notifications may be generated in response to detection of a predetermined event (e.g., upon detection that a parameter value has fallen below a user-designated predetermined threshold) and communicated to and exported by the data export module 125b at predetermined time intervals (e.g., every 30 minutes, hour, etc.). Additionally or alternatively, the alert/notifications may be generated and transmitted substantially immediately upon detection that an indicator value for a parameter has fallen outside of a predetermined threshold.

Figure 2:
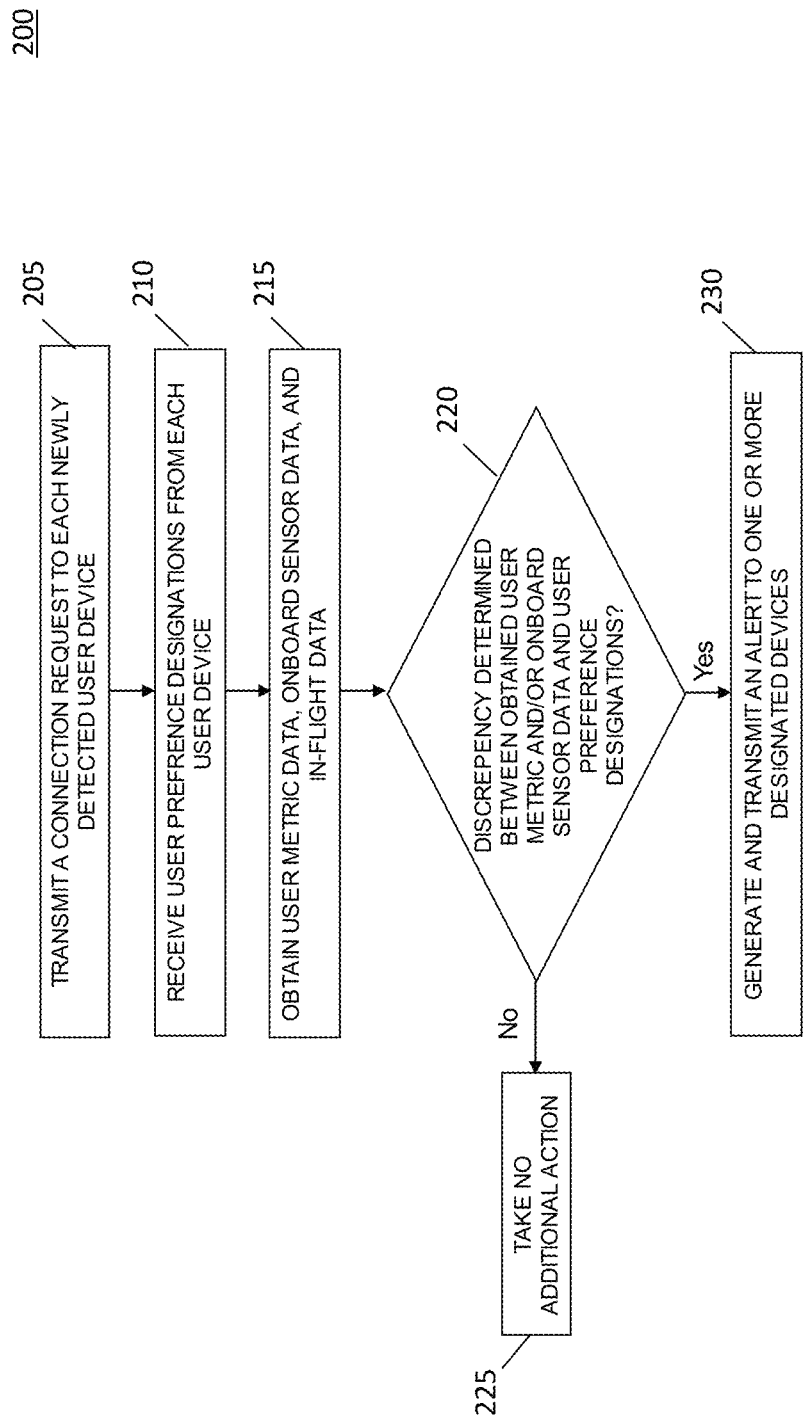
FIG. 2 depicts a flowchart of an exemplary method for transmitting a health/comfort alert, according to one or more embodiments of the present disclosure.

Turning now to FIG. 2, an exemplary process flow 200 is provided for generating passenger health and/or comfort alerts, according to one or more embodiments of the present disclosure. The exemplary process flow 200 may be implemented by environment 100 and the components thereof, as previously described above.

At step 205, the environment 100 may transmit a connection request notification to each newly detected user device. More particularly, each time the environment 100 detects that a new device has entered a predetermined space (e.g., the cabin of the aircraft, etc.), a notification requesting initial pairing and/or reconnection to the environment 100 may be transmitted to the user device (e.g., using one or more available device communication protocols, etc.). For first time users, the notification may contain functionality to enable the new users to create an account with the environment 100.

At step 210, the environment 100 may receive user preference designations from each user device. User preference designations include those parameters that a user wants tracked as well as their desired comfort levels for each parameter. For example, a user may desire to have a combination of internal and external parameters tracked such as sound, air temperature, air humidity, light exposure, water consumption/food patterns, sleep patterns, activity information, other type of parameters, etc. In an embodiment, for returning devices, the user preference designations may simply be transmitted from the user device to the environment 100. For new users, the environment 100 may guide a user through an interface through which the user may provide indications of the various user metrics and/or environmental parameters that they would like tracked and may further query the user to provide comfort thresholds for each parameter (e.g., a user may designate that they prefer the ambient temperature in their area of the flight cabin to be no less than 70 degrees Fahrenheit).

At step 215, the environment 100 may obtain a variety of different types of real-world data. In an embodiment, the real-world data may include user metric data, onboard sensor data, and/or in-flight data and may be obtained using the wearable data connector 110a, the in-flight sensor data connector 110b, and the flight data connector 110c, as previously described above.

At step 220, the environment 100 may determine whether a discrepancy is identified between any of the obtained real-world data types described above and the user preference designations. In this regard, the environment 100 may be determine whether the detected values for any real-world data articles fall outside of the user-designated comfort thresholds for one or more parameters that the user has indicated they wanted tracked. Responsive to determining, at step 220, that a discrepancy does not exist, an embodiment may, at step 225, take no additional action. More particularly, an embodiment may continue to monitor the real-world data values to determine if/when a discrepancy arises. Conversely, responsive to determining, at step 220, that a discrepancy does exist, an embodiment may, at step 230, generate and transmit an alert to one or more designated user devices.

In an embodiment, each of these alerts may, for example, identify the relevant passenger for which the alert was generated, provide an indication of the particular parameter(s) for the relevant passenger that have fallen below the predetermined threshold, and provide one or more recommendations for ways that the parameter value(s) may be adjusted back to a normal/optimal range. In an embodiment, the alerts may be transmitted to one or more user-designated devices (e.g., designated during pairing, etc.) such as a flight crewmember device, a device associated with an aviation fitness consultant, a device associated with the aircraft pilot, and the like. Non-limiting types of alerts may include those that indicate that: the sound is too loud in the cabin, the temperature is too hot or cold in the cabin in view of user preference designations, the user has slept less than their preferred amount or more than their preferred amount, the requested dining time for a user has arrived, etc.

Additionally or alternatively to the foregoing, the alerts may be anticipatory in nature. More particularly, the environment 100 may generate an alert prior to the real-world data conflicting with the user preference designations. For instance, responsive to identifying that the cabin sound levels are approaching a user-designated threshold, the environment 100 may generate an anticipatory alert and transmit it to the flight crew to turn the volume down inside the cabin down. In another example, the environment 100 may leverage the knowledge obtained from the real-world data to anticipate that the user may still be tired and/or jetlagged upon their arrival at the destination airport. Accordingly, the environment 100 may attempt to mitigate this anticipated discomfort by identifying characteristics of the destination airport (e.g., temperature, sounds levels, color schemes, etc.) and thereafter transmitting suggestions to the flight crew to try and gradually mimic these characteristics as the plane approaches the destination (e.g., by gradually increasing the sound, decreasing the temperature, adjusting cabin lighting, etc.).

Additionally or alternatively to the foregoing, the environment 100 may receive indications of the operational status and/or maintenance history of those in-flight components that may have an effect on passenger comfort (e.g., operational quality of air-conditioning unit, etc.). Those components known to be frequently relied on by passengers to mitigate their discomfort (e.g., the air-conditioning unit, in-flight monitors, etc.) may be assigned to a priority maintenance schedule over other components that may not be utilized as frequently. In an embodiment, the collective operability of these components may be used to create a comfort certification standard for which onboard equipment and services can be provided to all of the equipment manufacturers.

Figure 3:
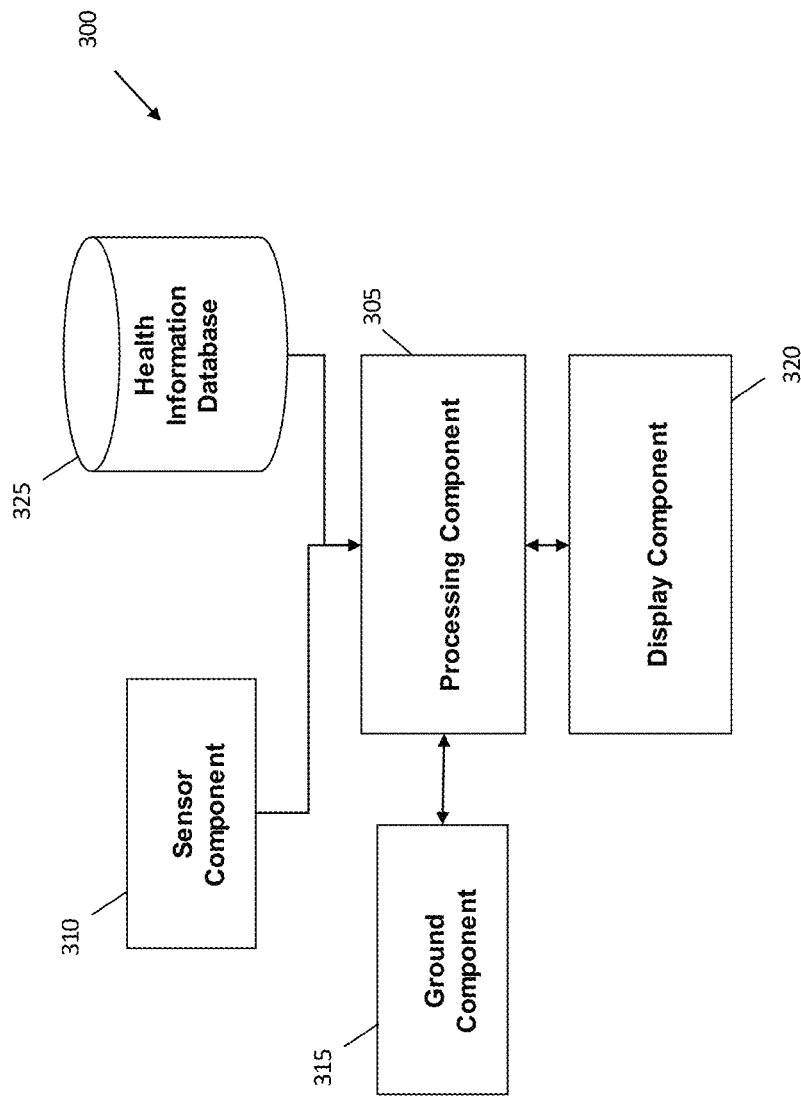
FIG. 3 depicts a system environment, according to one or more embodiments of the present disclosure.

Turning now to FIG. 3, an exemplary In-Flight Health Monitoring and Solution System ("system") is provided according to one or more embodiments of the present disclosure. The system 300 may include a processing component 305, a sensor component 310, a ground component 315, a display component 320, and a health information database component 325. In general, the collective components of the system may operate together to more efficiently monitor passenger health and react to medical emergencies.

In an embodiment, the processing component 305, which may be a "Health and Flight Profile Data Processor" (HFPDP), may be directly connected to each of the other components in the system 300. The HFPDP may process information received from each of the other components and may also relay information between components to maximize interoperability.

In an embodiment, the sensor component 310 may be operable to obtain health parameter data associated with a user from one or more connected sensors. In an embodiment, some or all of the sensors may be stand-alone sensors or, alternatively, some or all of the sensors may be integrated into another device (e.g., a wearable device such as a smart watch). Non-limiting examples of user health parameters that may be detected by the sensors include heart rate, respiration rate, body temperature, blood pressure, electrocardiogram (ECG) readings, sugar levels, and the like. In an embodiment, some or all of the sensors may be always on. Alternatively, some or all of the sensors may only initiate their sensing functionality in response to a predetermined event (e.g., upon detecting that a user has boarded a plane, upon detecting that a user has sat down in their seat, upon receiving an explicit command to activate, etc.).

In an embodiment, the ground component 315 may be operable to communicate information to and receive information from one or more ground-based facilities or contacts. In an embodiment, one potential ground-based facility may include a medical facility from which passenger medical history data may be obtained from. In another embodiment, the ground component 315 may have connectivity to one or more passenger emergency home contacts. The system 300 may leverage these contacts to not only apprise them of a struggling passenger's condition, but also to utilize their personal knowledge of the struggling passenger to minimize issues during aid administration (e.g., a family member may inform an aid administrator of allergic medicines that should be avoided, etc.). In an embodiment, contact with other ground facilities connectable to the ground component 315, such as the air-traffic controller (ATC) and/or the airport operations center (AOC), may facilitate faster identification and approval of a diversion location (e.g., an airport that a plane may be diverted in response to an onboard health emergency). Additionally, this information exchange may enable certain ground contacts (e.g., doctors, family members, etc.) to obtain priority ticketing to the diversion location.

In an embodiment, the display component 320 may be operable to display various types of information associated with the health emergency to one or more connected display devices. For example, the display component 320 may be configured to present an alert, e.g., to all crew member devices, when a passenger health emergency has been identified. In another example, the display component 320 may also present various types of information associated with the passenger experiencing the health emergency such as, for example, existing medical conditions, blood type, allergies, etc. In yet another example, the display component 320 may display aid administration/treatment instructions for the specific type of health emergency experienced by the affected passenger.

In an embodiment, the health information database 325 may contain medical data on each passenger that has subscribed to the system 300. In an embodiment, medical information may be added to the health information database by the passenger themselves (e.g., via interaction with a display associated with the display component 320). Additionally or alternatively, assuming appropriate authorizations, available medical information associated with each passenger may be pulled from a ground-based medical facility and then added to the health information database 320 dynamically (e.g., upon purchase of a ticket, upon flight boarding, etc.). In another embodiment, those passengers that are frequent flyers may have more robust medical records contained in the health information database 325 due to frequent pulling of their medical data from past flights. In an embodiment, medical data stored in the health information database 325 may be accessible at all points in-flight, regardless of whether any Internet connectivity exists. The continuous availability of this medical information may be useful to aid administrators, especially any doctors or nurses that may be onboard.

In an embodiment, the system 300 may be compatible with the application environment 100 onboard the same aircraft. More particularly, one or more aspects of the application environment 100 may be configured to run on the system 300. Additionally, in an embodiment, data obtained by one or more sensors associated with the sensor component 310 of the system 300 may be accessible to the application environment 100. Similarly, in another embodiment, passenger health data accessible to the application environment 100 may be shared with the system 300 and incorporated into the health information database 325.

Figure 4:
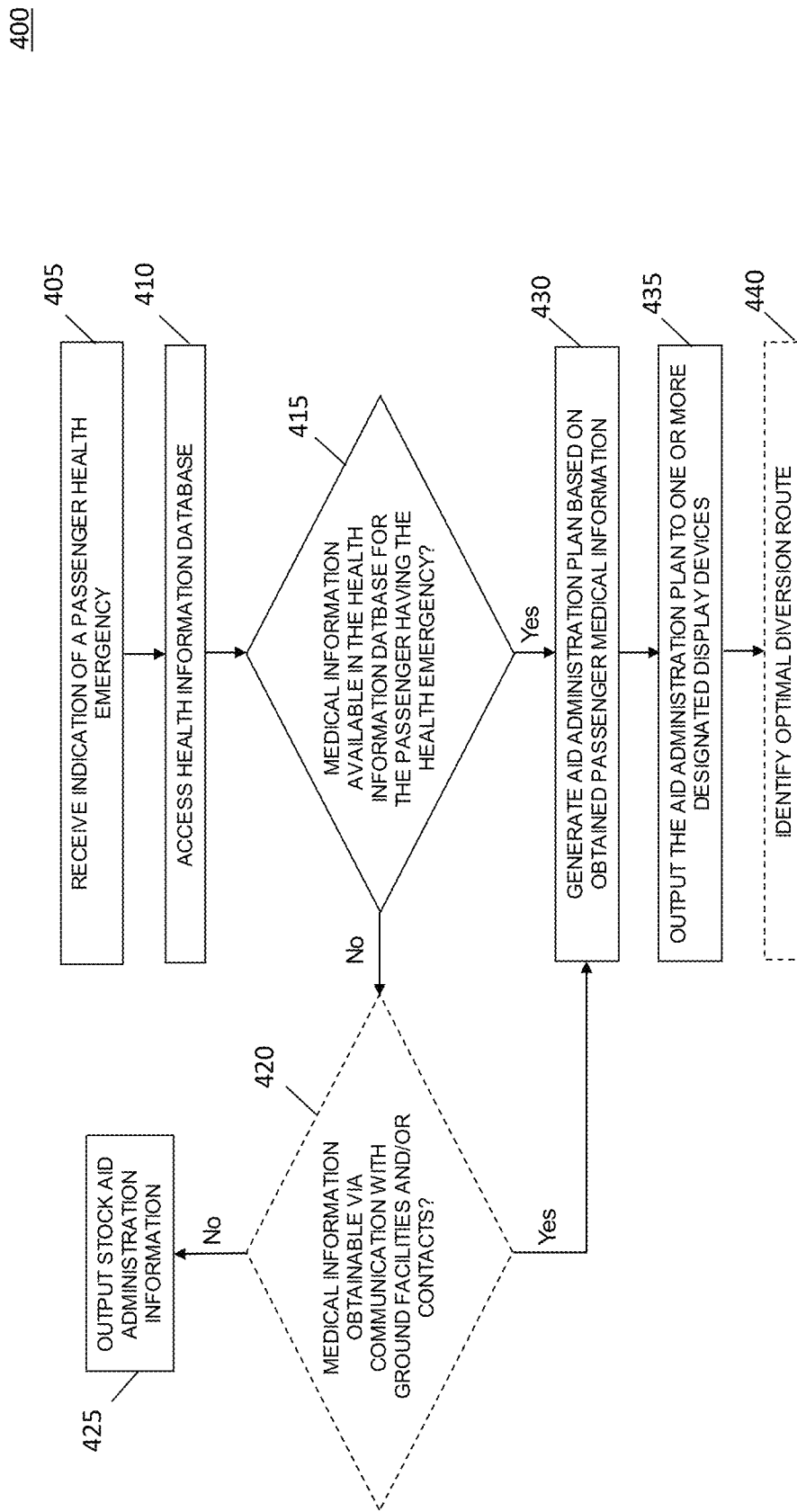
FIG. 4 depicts a flowchart of an exemplary method for generating an aid administration plan in response to a passenger health emergency, according to one or more embodiments.

Turning now to FIG. 4, an exemplary process flow 400 is provided for responding to a passenger health emergency, according to one or more embodiments of the present disclosure. The exemplary process flow 400 may be implemented by system 300 and the components thereof.

At step 405, the system 300 may receive an indication of a passenger health emergency. In an embodiment, the indication may be received manually (e.g., from a flight crew member, another passenger, the passenger experiencing the emergency themselves, etc.) via interaction with an onboard device associated with the system 300. Alternatively, in another embodiment, the indication may be detected dynamically. For example, one or more sensors associated with the sensor component 310 may be configured to continuously capture data and transmit that data to the processing component 305. Upon detecting, at the processing component 305, that received sensor data indicates that one or more health parameters of a passenger are outside of a normal threshold range, then the processing component 305 may conclude that a passenger health emergency is occurring. Alternatively to the foregoing, in another embodiment, the processing component 305 of the system 300 may not determine that an actual emergency exists until the relevant health parameter has remained outside of the normal threshold range for a predetermined period of time.

At step 410, upon determining that a passenger health emergency exists, the processing component 305 may access the health information database 325 to determine whether passenger-specific medical information is available for the passenger experiencing the health emergency. Responsive to determining, at 415, that the health information database 325 does not contain any medical information associated with the passenger, then an embodiment may output, at step 425, stock aid administration instructions to one or more display devices associated with the display component 320. In an embodiment, the stock aid administration instructions may correspond to conventional aid administration techniques that have historically been provided to passengers experiencing health emergencies during flight. Optionally, responsive to determining, at 415, that the health information database 325 does not contain any medical information associated with the passenger, then an embodiment may contact, at optional step 420, one or more ground facilities or contacts via the ground component 315 in an attempt to obtain medical information associated with the passenger. For example, the ground component 315 may attempt to contact one or more medical facilities (e.g., a default medical facility) and/or passenger family members to determine whether the passenger experiencing the health emergency has one or more pre-existing medical conditions, is allergic to certain medicines, etc. If no additional medical information may be obtained from the ground contacts, then an embodiment may output, at 425, stock aid administration information.

Responsive to determining, at step 415, that the health information database 325 does contain medical information associated with the passenger experiencing the health emergency and/or responsive to determining that passenger-based medical information has been received from a ground facility or contact, an embodiment may, at step 430, generate an aid administration plan based on the medical information associated with the relevant passenger. In this regard, the processing component may be integrated with, or have access to, a trained machine learning model that may be configured to process the sensor data and the medical information data to provide and thereafter construct a aid administration plan that is mindful of the passenger medical data (e.g., passenger allergies, sensitivities, existing health issues, etc.).

At step 435, the generated aid administration plan may be output to one or more designated display devices. For example, the aid administration plan may be transmitted to one or more devices of the flight crew. Additionally or alternatively, the aid administration plan may be readily accessible via any infotainment screen on board the plane (e.g., on each seat back, etc.). Additionally or alternatively, the aid administration plan may be transmitted to one or more ground contacts (e.g., doctors, other types of medical professionals, etc.) so that they may have an opportunity to review it and/or suggest alterations to the plan.

At optional step 440, the processing component 305 may determine that the passenger health emergency is severe enough to warrant a flight diversion. In such a scenario, the ground component 315 may initiate contact with one or more ground facilities, e.g., (ATC, AOC, etc.) to both, A) identify an optimal airport that the airplane may be diverted to (e.g., an airport that is proximate to a medical facility that may have the necessary facilities needed to care for the type of health emergency the patient is experiencing, etc.); and B) obtain prioritized clearance for the proposed diverted route.

Figure 5:
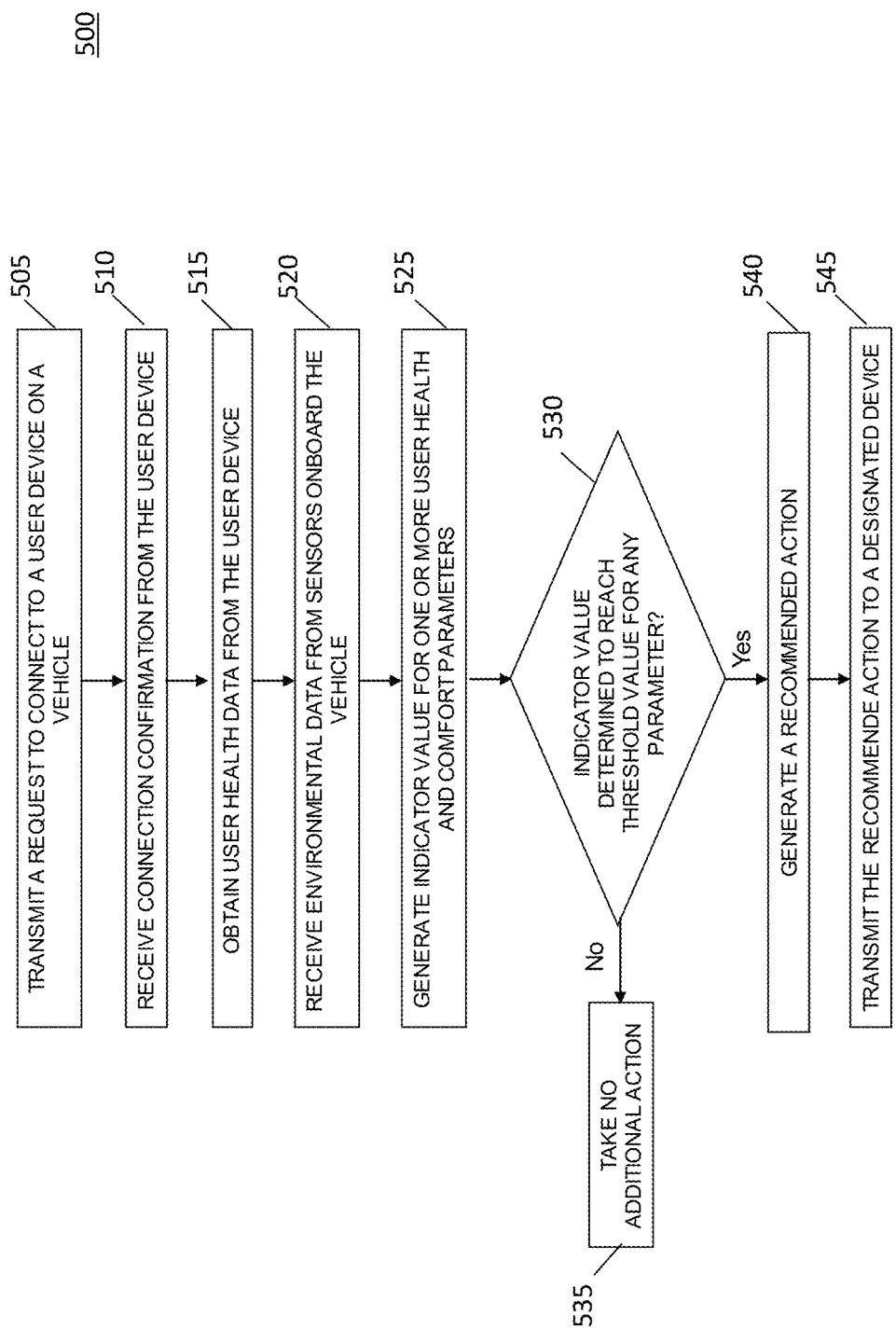
FIG. 5 depicts a flowchart of an exemplary method of monitoring and responding to passenger health, according to one or more embodiments.

Turning now to FIG. 5, an exemplary process flow 500 is provided for monitoring health information and providing recommendations for one or more passengers on a vehicle, according to one or more embodiments of the present disclosure. The exemplary process flow 500 may be implemented by application environment 100 and system 300, along with the components thereof.

At step 505, a health monitoring system associated with the aircraft may transmit a request to connect to a user device associated with a passenger. In an embodiment, the transmission may be facilitated automatically upon detecting that the user device has entered within a predetermined space (e.g., the cabin of the vehicle, the walkway to the vehicle, etc.). At step 510, the health monitoring system may monitor for receipt of a connection confirmation from the user device. In an embodiment, the connection confirmation may provide an indication that the user device has signed into or registered with the health monitoring system.

At step 515, once connected to the user device the health monitoring system may obtain passenger health data. In an embodiment, the passenger health data may correspond to one or more biometrics associated with the passenger (e.g., heart rate, respiration rate, body temperature, blood pressure, etc.). In an embodiment, the passenger health data may be obtained by one or more sensors integrally or operatively coupled to the user device, which may thereafter communicate that data to the health monitoring system. At step 520, the health monitoring system may receive environmental data from one or more other sensors located onboard the aircraft. In an embodiment, the environmental data may correspond to air quality of the cabin (e.g., air temperature, air humidity, etc.), ambient sound levels, ambient light levels, ambient movement levels, etc.

At step 525, the health monitoring system may generate an indicator value for each of a plurality of health and/or comfort parameters of the user based on the user health data and the environmental data. More particularly, given all of the sensor data obtained from the user device and the onboard sensors, the health monitoring system may derive an objective value each of the health and/or comfort parameters associated with a user.

At step 530, the health monitoring system may determine whether the indicator value has reached a threshold value for any of the parameters. In an embodiment, the threshold value may be a value designated by the passenger themselves (e.g., a temperature above which the user becomes too hot, a light level at which the user's eyes begin to hurt, etc.), or, alternatively may be a known medical value (e.g., an objective heart rate value known to be indicative of a serious issue, etc.).

Responsive to determining, at step 530, that the indicator value has not reached the threshold value for any of the parameters, an embodiment may, at step 535, take no additional action. Conversely, responsive to determining, at step 530, that the indicator value has reached the threshold value for at least one parameter, an embodiment may, at step 540, generate a recommended action and thereafter transmit, at step 545, the recommendation action to a designated device. In an embodiment, the designated device may correspond to one or more of: the passenger's device, a flight crewmembers device, an emergency services device (e.g., belonging to a medical professional in the vicinity of the passenger, belonging to a medical professional that may communicate with the passenger or flight crew, etc.), and a device of a designated contact of the passenger (e.g., certain friends or family members, etc.).

In an embodiment, if the threshold value corresponds to an emergency health condition and the indicator value reaches that threshold value for any of the parameters, then the generation of the recommended action may correspond to an aid-administration strategy that is optimized for the passenger and developed to directly address and/or mitigate the emergency health condition. In an embodiment, the development of the aid-administration strategy may be accomplished by obtaining any medical and/or personal information available for the passenger (e.g., stored in a medical history database accessible to the health monitoring system, etc.). Additionally or alternatively, the aid administration strategy may be developed by a trained machine learning model of the health monitoring system to directly address emergency health condition of the passenger. In this regard, the trained machine learning model may be provided with a compilation of input data such as passenger information (e.g., age, sex, etc.), passenger health data (e.g., allergies, existing health issues, etc.), the environmental data (e.g., cabin temperature, etc.), the indicator value itself, other types of relevant data, and the like. The trained machine learning model may there output a recommendation result for treating the emergency health condition of the passenger. Furthermore, in an embodiment, the health monitoring system may opt to institute a diversion to an original flight plan responsive to identifying that the emergency health condition is serious enough.

In an embodiment, if the threshold value corresponds to a minimum comfort value and the indicator value reaches the threshold value, then the generation of the recommended action may include identifying one or more aspects of the environmental data that can be adjusted (e.g., temperature, sound levels, light levels, etc.) and thereafter providing a recommendation for how these aspects can be adjusted to effectively move the indicator value away from the threshold value.

In general, any process discussed in this disclosure that is understood to be computer-implementable, such as the processes illustrated in FIGS. 2 and 4-5, may be performed by one or more processors of a computer server. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer server. A processor may be a central processing unit (CPU), a graphics processing unit (GPU), or any suitable types of processing unit.

A computer system may include one or more computing devices. If the one or more processors of the computer system are implemented as a plurality of processors, the plurality of processors may be included in a single computing device or distributed among a plurality of computing devices. If a computer server comprises a plurality of computing devices, the memory of the computer server may include the respective memory of each computing device of the plurality of computing devices.

Figure 6:
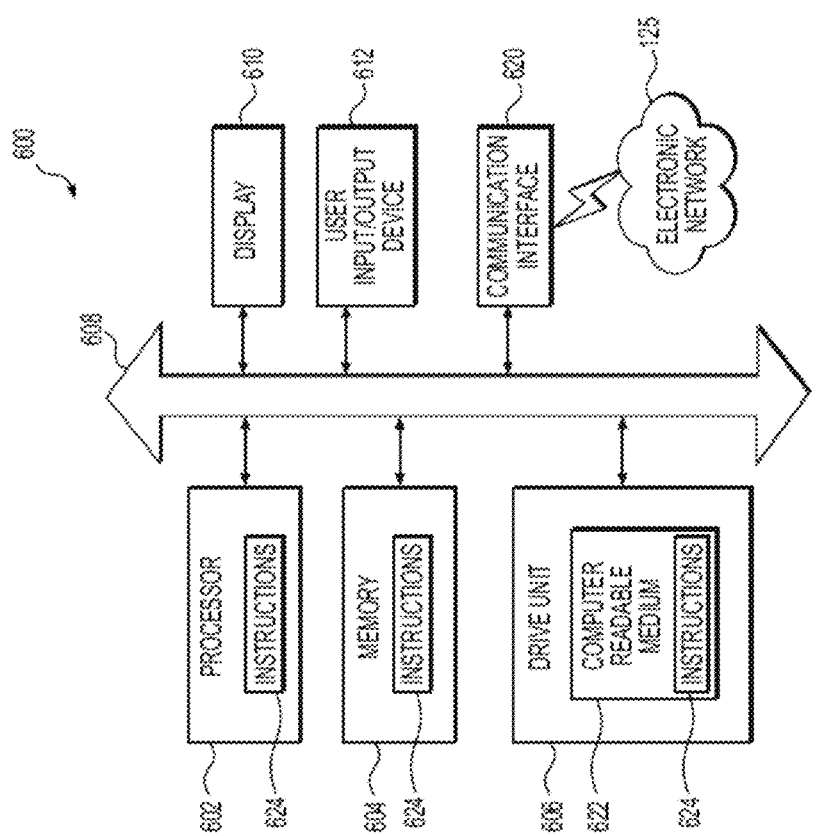
FIG. 6 depicts an exemplary computing server, according to one or more embodiments.

FIG. 6 is a simplified functional block diagram of a computer system 600 that may be configured as a computing device for executing the process illustrated in FIGS. 2 and 4-5, according to exemplary embodiments of the present disclosure. FIG. 6 is a simplified functional block diagram of a computer that may be configured as according to exemplary embodiments of the present disclosure. In various embodiments, any of the systems herein may be an assembly of hardware including, for example, a data communication interface 620 for packet data communication. The platform also may include a central processing unit ("CPU") 602, in the form of one or more processors, for executing program instructions. The platform may include an internal communication bus 608, and a storage unit 606 (such as ROM, HDD, SDD, etc.) that may store data on a computer readable medium 622, although the system 600 may receive programming and data via network communications. The system 600 may also have a memory 604 (such as RAM) storing instructions 624 for executing techniques presented herein, although the instructions 624 may be stored temporarily or permanently within other modules of system 600 (e.g., processor 602 and/or computer readable medium 622). The system 600 also may include input and output ports 612 and/or a display 610 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method of monitoring health information and providing recommendations for one or more passengers on a vehicle, the method comprising:

transmitting, from a health monitoring system associated with the vehicle, a request to connect to a user device associated with a passenger on the vehicle;

receiving, at the health monitoring system and from the user device, a connection confirmation;

obtaining, using the health monitoring system subsequent to receiving the connection confirmation and from one or more sensors associated with the user device, passenger health data for the passenger;

receiving, at the health monitoring system from one or more other sensors onboard the vehicle, environmental data that is associated with the passenger's environment;

generating, based on the passenger health data and the environmental data, an indicator value for each of a plurality of parameters;

determining, using a processor of the health monitoring system, that the indicator value for any of the plurality of parameters has reached a threshold value, wherein the threshold value corresponds to an emergency health condition;

obtaining medical or personal information available for the passenger;

generating, responsive to determining that the indicator value has reached the threshold value for any of the plurality of parameters, a recommended action, wherein the recommended action corresponds to an optimal aid-administration plan that is optimized for the passenger and developed to address the emergency health condition; and automatically transmitting the recommended action to a designated device.

2. The computer-implemented method of claim 1, wherein the threshold value corresponds to an emergency health condition of the passenger.

3. The computer-implemented method of claim 2, further comprising accessing, utilizing the health monitoring system, a database comprising passenger information associated with the one or more passengers, wherein the passenger information comprises at least one of: medical history information, family contact information, travel information, and work history information.

4. The computer-implemented method of claim 3, wherein the generating the recommended action comprises generating, via leveraging the passenger information, an optimal aid administration plan to address the emergency health condition.

5. The computer-implemented method of claim 4, wherein the generating the optimal aid administration plan comprises:
  providing, as input to a trained machine learning model, a compilation of input data comprising: the passenger information, the passenger health data, the environmental data, and the indicator value; and
  receiving, at the health monitoring system from the trained machine learning model, an output recommendation result comprising the recommended action.

6. The computer-implemented method of claim 2, further comprising instituting a modification to an original flight plan in view of the emergency health condition of the passenger.

7. The computer-implemented method of claim 1, wherein the threshold value corresponds to a minimum comfort value for any of the plurality of parameters as designated by the passenger.

8. The computer-implemented method of claim 7, wherein the threshold value is designated by the passenger.

9. The computer-implemented method of claim 7, wherein the generating the recommended action comprises:
  identifying one or more aspects of the environmental data that can be adjusted to move the indicator value away from the threshold value; and
  providing an adjustment level recommendation by which each of the one or more aspects can be adjusted.

10. The computer-implemented method of claim 1, wherein the designated device is at least one of: the user device, a crew-member device, an emergency services device, and a designated contact device.

11. A system for monitoring health information and providing recommendations for one or more passengers on a vehicle, comprising:
  at least on processor;
  at least one database; and
  a server in network communication with the at least one database, the server configured to perform operations including:
    transmitting, from a health monitoring system associated with the vehicle, a request to connect to a user device associated with a passenger on the vehicle;
    receiving, at the health monitoring system and from the user device, a connection confirmation;
    obtaining, using the health monitoring system subsequent to receiving the connection confirmation and from one or more sensors associated with the user device, passenger health data for the passenger;
    receiving, at the health monitoring system from one or more other sensors onboard the vehicle, environmental data that is associated with the passenger's environment;
    generating, based on the passenger health data and the environmental data, an indicator value for each of a plurality of parameters;
    determining, using a processor of the health monitoring system, that the indicator value for any of the plurality of parameters has reached a threshold value, wherein the threshold value corresponds to an emergency health condition;
    obtaining medical or personal information available for the passenger;
    generating, responsive to determining that the indicator value has reached the threshold value for any of the plurality of parameters, a recommended action, wherein the recommended action corresponds to an optimal aid-administration plan that is optimized for the passenger and developed to address the emergency health condition; and
    automatically transmitting the recommended action to a designated device.

12. The system of claim 11, wherein the threshold value corresponds to an emergency health condition of the passenger.

13. The system of claim 12, further comprising accessing, utilizing the health monitoring system, a database comprising passenger information associated with the one or more passengers, wherein the passenger information comprises at least one of: medical history information, family contact information, travel information, and work history information.

14. The system of claim 13, wherein the generating the recommended action comprises generating, via leveraging the passenger information, an optimal aid administration plan to address the emergency health condition.

15. The system of claim 14, wherein the generating the optimal aid administration plan comprises:
  providing, as input to a trained machine learning model, a compilation of input data comprising: the passenger information, the passenger health data, the environmental data, and the indicator value; and
  receiving, at the health monitoring system from the trained machine learning model, an output recommendation result comprising the recommended action.

16. The system of claim 12, further comprising instituting a modification to an original flight plan in view of the emergency health condition of the passenger.

17. The system of claim 11, wherein the threshold value corresponds to a minimum comfort value for any of the plurality of parameters as designated by the passenger.

18. The system of claim 17, wherein the generating the recommended action comprises:
  identifying one or more aspects of the environmental data that can be adjusted to move the indicator value away from the threshold value; and providing an adjustment level recommendation by which each of the one or more aspects can be adjusted.

19. The system of claim 11, wherein the designated device is at least one of:
the user device, a crew-member device, an emergency services device, and a designated contact device.

20. A non-transitory computer-readable medium storing computer-executable instructions which, when executed by a server in network communication with at least one database, cause the server to perform operations comprising:
transmitting, from a health monitoring system associated with a vehicle, a request to connect to a user device associated with a passenger on the vehicle;
receiving, at the health monitoring system and from the user device, a connection confirmation;
obtaining, using the health monitoring system subsequent to receiving the connection confirmation and from one or more sensors associated with the user device, passenger health data for the passenger;
receiving, at the health monitoring system from one or more other sensors onboard the vehicle, environmental data that is associated with the passenger's environment;
generating, based on the passenger health data and the environmental data, an indicator value for each of a plurality of parameters;
determining, using a processor of the health monitoring system, that the indicator value for any of the plurality of parameters has reached a threshold value, wherein the threshold value corresponds to an emergency health condition;
obtaining medical or personal information available for the passenger;
generating, responsive to determining that the indicator value has reached the threshold value for any of the plurality of parameters, a recommended action, wherein the recommended action corresponds to an optimal aid-administration plan that is optimized for the passenger and developed to address the emergency health condition; and
automatically transmitting the recommended action to a designated device.

* * * * *